United States Patent [19]

Frank

[11] 4,228,100
[45] Oct. 14, 1980

[54] QUATERNARY UREIDOMETHYL PHOSPHONIUM SALTS

[75] Inventor: Arlen W. Frank, Slidell, La.

[73] Assignee: The United States of America as represented by the Secretary of Agriculture, Washington, D.C.

[21] Appl. No.: 27,696

[22] Filed: Apr. 6, 1979

[51] Int. Cl.³ .................. C07F 9/22; C07C 127/15; C09K 3/28
[52] U.S. Cl. .................. 260/551 P; 260/239 EP; 260/553 R; 260/553 A; 427/353; 427/394
[58] Field of Search ............ 260/551 P, 553 R, 553 A

[56] References Cited

U.S. PATENT DOCUMENTS

| | | | |
|---|---|---|---|
| 2,772,188 | 11/1956 | Reeves et al. | 260/551 P X |
| 2,812,311 | 11/1957 | Reeves et al. | 260/551 P UX |
| 2,983,623 | 5/1961 | Coates . | |
| 3,878,245 | 4/1975 | Nachbur et al. | 260/553 R |
| 3,931,310 | 1/1976 | Nachbur et al. | 260/551 P |
| 3,980,618 | 9/1976 | Birum | 260/551 P |
| 3,994,971 | 11/1976 | Nachbur et al. | 260/551 P X |
| 4,102,923 | 7/1978 | Pepperman, Jr. et al. | 260/553 R |

FOREIGN PATENT DOCUMENTS

| | | |
|---|---|---|
| 740269 | 11/1955 | United Kingdom . |
| 761985 | 11/1956 | United Kingdom . |
| 1372920 | 11/1974 | United Kingdom ................ 260/551 P |

OTHER PUBLICATIONS

Nachbur et al., CA 79:20253u, 20254v, 20255w, (1973).
Donaldson et al., CA 84:137077j, (1976).
Kasem et al., J. Appl. Polymer Sci. 15, 2237-2243, (1971).
Pepperman, Jr. et al., J. Org. Chem. 41, 675-678, (1976).

*Primary Examiner*—Thomas A. Waltz
*Attorney, Agent, or Firm*—M. Howard Silverstein; David G. McConnel; Raymond C. Von Bodungen

[57] ABSTRACT

Novel quaternary ureidomethyl phosphonium salts having the general formula

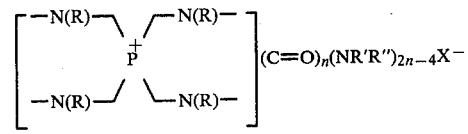

are prepared by condensing a urea having the formula RNHC(O)NR'R" with a quaternary hydroxymethyl phosphonium salt having the formula $(HOCH_2)_4P^+X^-$ in a molar ratio of at least 2:1. The products, which are characterized by the absence of residual hydroxymethyl groups, are useful as finishing agents for imparting flame retardant properties to cotton fabrics.

25 Claims, No Drawings

QUATERNARY UREIDOMETHYL PHOSPHONIUM SALTS

BACKGROUND OF THE INVENTION

1. Field of the Invention

This invention relates to novel quaternary phosphonium salts, and to methods for the preparation thereof. More particularly it relates to novel quaternary phosphonium salts in which each and every phosphorus atom bears a ureidomethyl substituent.

2. Description of the Prior Art

Polymers based on tetrakis(hydroxymethyl)phosphonium salts such as the chloride (THPC) and more recently the sulfate (THPS) are used extensively in flame retardant finishes for cotton (J. W. Lyons, "The Chemistry and Uses of Fire Retardants," Wiley-Interscience, New York, 1970, pp 189-208). The phosphonium salt, partially neutralized with a base such as triethanolamine or sodium hydroxide to prevent premature polymerization, is applied to the cotton with a multifunctional nitrogen compound such as urea or melamine and heat cured (THPC/amide process, or it is applied to the cotton by itself and ammonia cured (THPOH/ammonia process). In either case, the use of a base or buffer causes the phosphonium salt to dissociate to tris(hydroxymethyl)phosphine (THP) and formaldehyde, resulting in a finish that no longer has a quaternary phosphonium structure. THPC/urea, THPC/melamine, and THPC/ammonia polymers prepared in the solid phase or in solution lose some formaldehyde and all of the chlorine, indicating conversion of the THPC to THP [M. A. Kasem et al., J. Appl. Polym. Sci., 15, 2237 (1971)]. The presence of trivalent phosphorus in several THPC/amide and THPOH/ammonia finishes has been established by iodometric titration [D. J. Daigle et al., J. Fire Flam., 1, 178 (1970)].

In one variant of the THPOH/ammonia process, a precondensate of urea and THPC is prepared by condensing the reagents in a 0.5:1 molar ratio prior to application of the finish to the cotton (PROBAN process). Such precondensates fall outside the scope of the present invention because they contain residual hydroxymethyl groups. In fact, the retention of at least one free methylol (i.e., hydroxymethyl) group per phosphorus atom is considered essential for the precondensate to retain its polymer-forming ability [W. A. Reeves and J. D. Guthrie, U.S. Pat. No. 2,772,188 (1956); H. Coates, U.S. Pat. No. 2,983,623 (1961)].

Condensation of THPC with 1,1-diphenylurea gives a quaternary ureidomethyl phosphonium salt having properties similar to some of those of the present invention, but alkyl ureas such as 1,1-dimethylurea or ethylurea are said to yield only intractable oils [A. B. Pepperman, Jr. et al., J. Org. Chem., 41, 675 (1976)]. Moreover, TKP, a phosphate/acetate salt similar to THPC, is said not to react with 1,3-dimethylurea under the conditions used to prepare the precondensate with urea [A. Granzow, J. Amer. Chem. Soc., 99, 2648 (1977)].

SUMMARY OF THE INVENTION

This invention relates to novel quaternary ureidomethyl phosphonium salts having the general formula

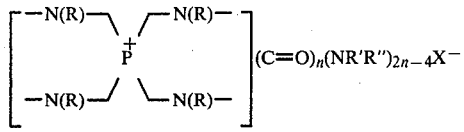

where R, R' and R" are hydrogen, alkyl, or substituted alkyl radicals, n is an integer from 2 to 4, and X is an acid radical, to processes for the preparation thereof, and to processes for employing the phosphonium salts for imparting flame-retardant character to cellulosic textiles.

It is the principal object of the invention to describe quaternary phosphonium salts in which each and every phosphorus atom bears a ureidomethyl substituent, i.e. in which the quaternary phosphonium salt contains no residual hydroxymethyl groups. The presence of hydroxymethyl groups renders quaternary phosphonium salts, and any tertiary phosphines, tertiary phosphine oxides, and polymeric products derived therefrom, sensitive to attack by alkali, resulting in hydrolytic cleavage, generation of hydrogen gas, or both. It is an object of the invention to demonstrate that quaternary ureidomethyl phosphonium salts (even those containing free N—H groups) do not generate hydrogen gas upon exposure to alkali. The difference in behavior between substances containing O—H and N—H groups is not at all obvious, even to those skilled in the art.

Other objects of the invention will become obvious from the detailed description of the preferred embodiments of the invention.

DESCRIPTION OF THE PREFERRED EMBODIMENTS

The novel quaternary ureidomethyl phosphonium salts of this invention have the general formula

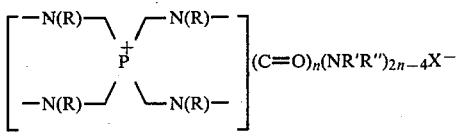

where R, R', and R" are hydrogen, alkyl, or substituted alkyl radicals, n is an integer from 2 to 4, and X is an acid radical.

In accordance with the practice of the invention, the new substances are prepared by condensing a urea having the general formula RNHC(O)NR'R" with a quaternary hydroxymethyl phosphonium salt having the general formula $(HOCH_2)_4P^+X^-$, wherein R, R', R" and X are as defined above, in a molar ratio of at least 2:1, and recovering the product from the resulting reaction mixture. The condensation is embodied in the following equation:

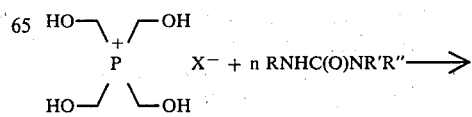

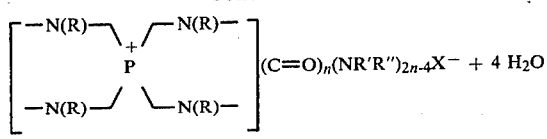

The ureas employed in the practice of this invention are exemplified by urea itself, N-methylurea, N-ethylurea, N-butylurea, 1,3-dimethylurea, 1,3-diethylurea, 1-ethyl-3-methylurea, 1,1-dimethylurea, N,N'-ethyleneurea (2-imidazolidinone), 1,3-bis(methoxymethyl)urea, and the like.

The quaternary hydroxymethyl phosphonium salts employed in the practice of this invention are exemplified by tetrakis(hydroxymethyl)phosphonium chloride (THPC), octakis(hydroxymethyl)diphosphonium sulfate (THPS), octakis(hydroxymethyl)diphosphonium oxalate, tetrakis(hydroxymethyl)phosphonium benzenesulfonate, and the like.

The condensation between the urea and the quaternary hydroxymethyl phosphonium salt can be carried out at temperatures ranging from 50° C. to 175° C., the preferred range being from 75° C. to 150° C. The condensation is usually performed at atmospheric pressure, but may also be performed at higher or lower pressures. A solvent may be employed, such as water, ethanol, butanol, benzene, toluene, xylene, and the like. In one of the preferred embodiments, the water formed in the condensation is removed by azeotropic distillation with toluene as it is formed, enabling the progress and the extent of completion of the reaction to be easily measured.

The structure of the product is profoundly influenced by the molar ratio of the reagents employed in the condensation. If the molar ratio of urea to quaternary hydroxymethyl phosphonium salt is 4:1 or higher, the product is a tetrakis(ureidomethyl)phosphonium salt containing four ureido substituents per phosphorus atom. Its structure, defined by n=4, is shown in formula I:

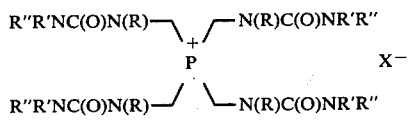

Products of this type in which R, R', and R" are H or CH₃ and X is Cl, Br, I, HSO₃, SO₃C₆H₅ or SO₃C₆H₄CH₃-p are air-stable, water-soluble compounds. Unlike THPC or THPS, the products are neutral in aqueous solution and do not generate hydrogen gas when treated with 50% sodium hydroxide. Some illustrations of these condensations are given in Examples 1 to 18.

If the molar ratio of urea to quaternary hydroxymethyl phosphonium salt is 2:1, the product is a bis(ureylenedimethyl)phosphonium salt containing two ureylene substituents per phosphorus atom. [In this context, the prefix ureido is used to denote the univalent radical H₂NC(O)NH— and the prefix *ureylene* to denote the bivalent radical —NHC(O)NH—, in accordance with IUPAC rules of nomenclature; see Chem. Abstr., 41, 5948 (1945)]. Its structure, defined by n=2, is either spiran or polymeric, or some combination thereof. The spiran structure is shown in formula II:

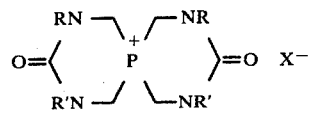

Products of this type in which R and R' are CH₃ and X is Cl, HSO₄ or SO₃C₆H₅ are water-soluble crystalline solids whose spiran structure is readily established by spectroscopic and analytical methods. Some illustrations of these condensations are given in Examples 19 to 21.

The polymeric structure is shown in formula III:

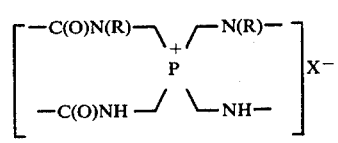

Products of this type in which R is H or CH₃ and X is Cl or SO₄ are friable white solids whose polymeric structure is inferred from their insolubility in water and organic solvents. Illustrations of these condensations are given in Examples 22 to 25.

If the molar ratio of urea to quaternary hydroxymethyl phosphonium salt is 3:1, the product is a bis(ureidomethyl)(ureylenedimethyl)phosphonium salt containing two ureido substituents and one ureylene substituent per phosphorus atom. Its structure, defined by n=3, is intermediate between those of n=2 and n=4, but the physical properties resemble those of n=2. The cyclic structure is shown in formula IV:

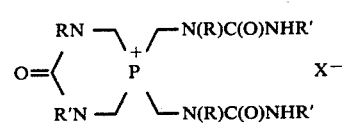

A product of this type in which R and R' are CH₃ and X is Cl is a water-soluble crystalline solid whose cyclic structure is readily established by spectroscopic and analytical methods. An illustration of this condensation is given in Example 26.

The polymeric structure is shown in formula V:

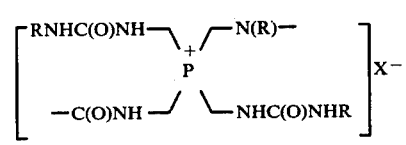

A product of this type in which R is H and X is Cl is a friable white solid whose polymeric structure is inferred from its insolubility in water and organic solvents. An illustration of this condensation is given in Example 27.

If the tetrakis(hydroxymethyl)phosphonium salt employed in these condensations is a salt of a dibasic acid, such as sulfuric acid or oxalic acid, the molar quantity of the salt taken into the reaction must be halved. Thus, the condensation of urea with THPC requires molar ratios of 4:1, 3:1, and 2:1 to give products of structure I, V, and III, respectively, whereas THPS requires molar ratios of 4:0.5, 3:0.5, and 2:0.5, respectively. If the tetrakis(hydroxymethyl)phosphonium salt is a salt of a tribasic acid, such as phosphoric acid or citric acid, the molar quantity of the salt taken into the reaction must be reduced to one-third; and so forth.

The phosphonium salts I, III, and V are interconvertible. Polymers of structure III, for example, can be prepared by condensing THPC, THPS, and the like with phosphonium salts of structure I. Conversely, polymers of structure III condense with urea, N-methylurea, and the like giving water-soluble phosphonium salts of structure I. Some illustrations of these interconversions are given in Examples 28 to 30.

The latter condensation provides a key step in the scale-up of the synthesis of tetrakis(ureidomethyl)phosphonium salts such as the sulfate (I, $R=R'=R''=H$, $X=0.5 SO_4$). Heating a mixture of urea and THPS in a 4:0.5 molar ratio is impractical because the reaction is too exothermic. Adding the THPS in increments to a hot aqueous urea solution is impractical because urea tends to hydrolyze in hot water, particularly when concentrated, releasing ammonia and carbon dioxide, and ammonia causes THPS to decompose, liberating phosphine. This problem can be solved, however, by adding the urea in increments to hot aqueous THPS solution. A water insoluble gel forms as the composition approaches $n=2$, remains insoluble through $n=3$, and gradually redissolves as the composition approaches $n=4$. This technique is illustrated in Example 31.

The cyclic phosphonium salts II and IV are also interconvertible. Cyclic phosphonium salts of structure IV, for example, can be prepared by condensing spirophosphonium salts of structure II with 1,3-dimethylurea and the like. This reaction is illustrated in Example 32. All such interconversions are not possible, however, for efforts to condense IV with 1,3-dimethylurea to give I, or THPC with I to give II, did not produce the desired results.

Quaternary ureidomethyl phosphonium salts having different X groups can be prepared either by ion exchange, or by the use of quaternary hydroxymethyl phosphonium salts which already have different X groups. Ion exchange may be accomplished by metathesis with a salt such as sodium iodide or barium chloride, by precipitation with an acid such as picric acid, by passage over an ion exchange resin, and the like. Some illustrations of these methods are given in Examples 33 to 35. The use of an ion exchange resin to purify quaternary ureidomethyl phosphonium salts is illustrated in Examples 10 and 11.

The novel compounds of this invention can be applied as finishing agents to cotton fabrics, imparting flame retardant properties thereto, but it is necessary to modify the customary pad/dry/cure technique somewhat in order to preserve the quaternary structure of the compounds. This is illustrated in Examples 36 to 39. Application of the urea/THPC finish to cotton printcloth at 160° C. (Table III) results in significant polymer fixation, particularly when the molar ratio approaches the 2:1 composition of structure III, but the chlorine is lost, showing that the structure is no longer quaternary. Little polymer fixation occurs under these conditions at curing temperatures below 140° C.

Application of the urea/THPS finish to cotton at 100° C., however, achieves the desired results, for these conditions resemble those employed in the synthesis of the compounds of this invention. Two methods of application are illustrated. In Examples 40 to 52, a 1:1 molar mixture of octakis(ureidomethyl)diphosphonium sulfate and THPS is applied to cotton printcloth at various curing times (Table IV) and curing temperatures (Table V) under conditions resembling those of Example 28. A cure time of 8 minutes at 100° C. is sufficient, and the quaternary structure of the polymer is retained. In Examples 53 to 57, a 2:0.5 molar mixture of urea and THPS is applied to cotton printcloth at various curing times (Table VI) under conditions resembling those of Example 24. The curing time must be extended to 32 minutes to achieve a comparable finish.

The following examples are given to illustrate the preparation and properties of the novel compounds of this invention and their use as flame retardants for cotton, and should not be construed as limiting the scope of the invention. Melting points were corrected. Infrared (IR) spectra were taken on a Perkin-Elmer 137B (w=weak, m=medium, s=strong, vs=very strong, br=broad). Nuclear magnetic resonance (NMR) spectra were taken on a Varian A-60A or Varian EM-360L, using TMS or DSS as an internal reference ($^1$H spectra), or a JEOL C-60-HL at 24.3 MHz, using 85% $H_3PO_4$ as an external reference ($^{31}$P spectra). Chemical shifts ($\delta$) downfield of the reference are positive. Electron spectroscopy for chemical analysis (ESCA) spectra were taken on a Varian IEE-15 equipped with a magnesium anode, the sample being mounted on a holder with double-backed adhesive tape. Fabric samples were analyzed by the X-ray fluorescence method (Cl, P and S) or by the Kjeldahl method (N); all other samples were analyzed by commercial laboratories.

EXAMPLE 1

A mixture of THPC (9.53 g, 0.05 mol), 1,3-dimethylurea (17.62 g, 0.20 mol), and toluene (75 ml) was heated to reflux in an apparatus fitted with a Dean-Stark trap for azeotropic removal of the water. The mixture was held at reflux until the evolution of water ceased; 3.7 ml (0.20 mol) was collected in 1 hr., and no more passed over in the next hr. The product, which had separated during the reaction as a mass of white solids, was broken up, triturated under toluene, filtered, and dried, giving 22.88 g (97.2%) of tetrakis(1,3-dimethylureidomethyl)phosphonium chloride (I, $R=R'=CH_3$, $R''=H$, $X=Cl$) as a white crystalline solid, mp 187°–189° C. dec. Two recrystallizations from 2-propanol (8 ml/g), followed by drying under vacuum for 2 hr at 56° C. (acetone), gave a 1:1 solvate of the product and 2-propanol, mp 194°–194.5° C. dec.

Anal. Calcd for $C_{19}H_{44}ClN_8O_5P$: C, 42.84; H, 8.09; Cl, 6.86; N, 20.95; P, 5.84. Found: C, 42.97; H, 8.35; Cl, 6.68; N, 21.11; P, 5.83.

Spectra: IR (Nujol) 950w $cm^{-1}$; $^1$H NMR (dmso-d$_6$) $\delta$ 1.06 (doublet, 6H, CH$_3$, J=6.0 Hz) ppm.

Further drying under vacuum for 4 hr at 100° C. (water) gave the solvent-free product as a white, crystalline solid, mp 194°–194.5° C. dec.

Anal. Calcd for $C_{16}H_{36}ClN_8O_4P$: C, 40.63; H, 7.83; Cl, 7.73; N, 23.62; P, 6.75; mol wt, 471. Found: C, 40.80; H, 7.71; Cl, 7.53; N, 23.80; P, 6.58; mol wt (osmometric in H$_2$O), 274,286.

Spectra: IR (Nujol) 720w, 770m, 815w, 854w, 877w, 892w, 1010w, 1080m, 1145m, 1235m, 1270m, 1290m, 1350s,sh, 1540vs (NH, amide II), 1630s and 1650vs (C=O, amide I), and 3300m (NH) $cm^{-1}$; $^1$H NMR data given in Table I; $^{31}$P NMR (H$_2$O) $\delta$ 32.0 ppm.

The phosphonium salt is soluble in water, the lower alcohols, and dimethylsulfoxide, and insoluble in other common organic solvents. The solvate is not formed when the product is just rinsed or rubbed with 2-propanol.

EXAMPLE 2

For large-scale preparation of tetrakis(1,3-dimethylureidomethyl)phosphonium chloride (I, R=R'=CH$_3$, R''=H, X=Cl), it is convenient to modify the procedure of Example 1 as follows. THPC is added in the form of its commercially available 80% aqueous solution drop by drop to a preheated solution of 1,3-dimethylurea in toluene, and the water is removed by azeotropic distillation as the reaction proceeds. On a 2.5 mol scale, the yield of product, mp 191°–192° C. dec, was 921 g (78.2%).

EXAMPLE 3

A solution of 80% THPC (59.55 g, 0.25 mol) and 1,3-dimethylurea (88.12 g, 1 mol) was heated to reflux in an oil bath, held at reflux for 4 hrs., allowed to cool, and stripped to dryness in a rotary evaporator. The residue (130.67 g) was shaken with acetonitrile (100 ml) and filtered, giving 29.40 g (25.0%) of tetrakis(1,3-dimethylureidomethyl)phosphonium chloride (I, R=R'=CH$_3$, R''=H, X=Cl) as a white, crystalline solid, mp 189°–190° C. dec. The remainder, a heavy oil, yielded no more product nor water even when subjected to azeotropic distillation with toluene and more 1,3-dimethylurea.

(NH) cm$^{-1}$; $^1$H NMR data given in Table I; $^{31}$P NMR (H$_2$O) δ 31.5 ppm.

EXAMPLE 5

Reaction of THPS (20.31 g, 0.05 mol) with 1,3-dimethylurea (35.25 g, 0.4 mol) in toluene (150 ml), following Example 1, gave 31.05 g (116.6%) of tetrakis(1,3-dimethylureidomethyl)phosphonium bisulfate (I, R=R'=CH$_3$, R''=H, X=HSO$_4$) as a white, crystalline solid, mp 175° C. dec after two recrystallizations from ethanol. An analytical sample was dried under vacuum for 4 hr at 100° C.

Anal. Calcd for C$_{16}$H$_{37}$N$_8$O$_8$PS: C, 36.08; H, 7.00; N, 21.05; P, 5.82; S. 6.02. Found: C, 35.90; H, 7.23; N, 19.91; P, 5.59; S, 5.60.

Spectra: IR (Nujol) 768w, 862w, 982w, 1045m, 1075w, 1140m,br, 1160m, 1220m, 1260w, 1350m, 1525vs (NH, amide II), 1620s (C=O, amide I), and 3230m (NH) cm$^{-1}$; $^1$H NMR data given in Table I; $^{31}$P NMR (H$_2$O) δ 30.9 ppm.

The phosphonium salt is soluble in water (pH 2.5), methanol, and dimethylsulfoxide, and insoluble in other common organic solvents. It can be recrystallized from ethanol (2 ml/g) or n-butanol (4 ml/g), forming 1:1 solvates which retain solvent tenaciously.

The product contained only one of the two phosphorus atoms of the THPS. The remainder of the product was a yellow oil (17.40 g) which comprised several

TABLE I

| | | $^1$H NMR Spectra of Phosphonium Salts$^a$ | | | | | |
|---|---|---|---|---|---|---|---|
| Example | Structure | Solvent | 3-CH$_3$ | 1-CH$_3$ | CH$_2$ | NH | X |
| 1 | I | (CD$_3$)$_2$SO | 2.63 (4.0)$^b$ | 2.98 (2.0) | 3.77 (4.0) | 7.02 (4.0)$^c$ | ... |
| 4 | I | " | 2.63 (4.0)$^b$ | 2.97 (1.0) | 3.76 (4.0) | 6.78 (4.0)$^c$ | ... |
| 5 | I | " | 2.61 (4.0)$^b$ | 2.93 (1.5) | 3.78 (4.5) | 6.87 (5)$^c$ | ... |
| 6 | I | D$_2$O | 2.72 | 2.95 (2.0) | 3.89 (4.0) | — | 7.57$^d$ |
| 7 | I | " | 2.75 | 2.97 (1.5) | 3.92 (4.0) | — | 2.39$^e$,7.55$^f$ |
| 8 | I | " | 2.96 | ... | 4.30 (3.5) | — | ... |
| 10 | I | " | 2.68 | ... | 4.25 (4.0) | — | ... |
| 11 | I | " | ... | ... | 4.25 (4.0) | — | ... |
| 13 | I | " | ... | ... | 4.21 (3.5) | — | ... |
| 19 | II | (CD$_3$)$_2$SO | ... | 2.89 (2.5) | 4.55 (9.0) | ... | ... |
| 20 | II | D$_2$O | ... | 2.97 (2.0) | 4.38 (8.0) | ... | ... |
| 26 | IV,ring$^g$ | " | ... | 2.90 (2.0) | 4.26 (6.5) | ... | ... |
| | —,chain | | 2.74 | 2.99 (2.0) | 3.90 (8.0) | — | ... |
| 34 | I | (CD$_3$)$_2$CO | 2.72 | 3.07 (2.0) | 3.83 (4.5) | 4.45$^c$ | 8.84$^h$ |

$^a$Chemical shifts (δ) in ppm and coupling constants (J) in Hz. All couplings are doublets unless otherwise noted.
$^b$Collapsing to singlet with D$_2$O.
$^c$Vanishing with D$_2$O.
$^d$Multiplet, C$_6$H$_5$.
$^e$Singlet, p-CH$_3$.
$^f$AB quartet, C$_6$H$_4$, Δ$_{AB}$ = 21.9 Hz, J$_{AB}$ = 8.5 Hz.
$^g$Assignments made by comparing the data of Examples 1, 19 and 26.
$^h$Doublet, m-C$_6$H$_2$.

EXAMPLE 4

Reaction of tetrakis(hydroxymethyl)phosphonium iodide (7.05 g, 0.025 mol) with 1,3-dimethylurea (8.81 g, 0.1 mol) in toluene (25 ml), following Example 1, gave 13.65 g (97.1%) of tetrakis(1,3-dimethylureidomethyl)-phosphonium iodide (I, R=R'=CH$_3$, R''=H, X=I) as a white, crystalline solid, mp 194° C. dec after two recrystallizations from ethanol (10 ml/g). The product suffered no weight loss when dried under vacuum for 2 hr at 100° C.

Anal. Calcd for C$_{16}$H$_{36}$IN$_8$O$_4$P: C, 34.17; H, 6.45; I, 22.56; N, 19.93; P, 5.51. Found: C, 34.17; H, 6.35; I, 22.79; N, 19.81; P, 5.56.

Spectra: IR (Nujol) 720w, 759s, 851w, 884m, 1005w, 1075m, 1150m, 1170m, 1230s, 1255m, 1280m, 1530vs,br (NH, amide II), 1640vs (C=O, amide I), and 3330s unidentified phosphorus-containing species and gave a positive test for P(III) with iodine.

Spectrum: $^{31}$P NMR (H$_2$O, decoupled, relative peak heights in brackets) δ 12.1 (31), 30.8 (100), 39.0 (14), and 48.6 (14) ppm.

EXAMPLE 6

Reaction of tetrakis(hydroxymethyl)phosphonium benzenesulfonate (15.61 g, 0.05 mol) with 1,3-dimethylurea (17.62 g, 0.2 mol) in toluene (200 ml), following Example 1, gave 21.91 g (73.9%) of tetrakis(1,3-dimethylureidomethyl)phosphonium benzenesulfonate (I, R=R'=CH$_3$, R''=H, X=SO$_3$C$_6$H$_5$) as a white, crystalline solid, mp 103°–105° C. after three recrystallizations from acetonitrile (3 ml/g). The analytical sample, dried under vacuum for 4 hr at 56° C. (acetone), analyzed as a hydrate.

Anal. Calcd for $C_{22}H_{41}N_8O_7PS \cdot H_2O$: C, 43.26; H, 7.10; N, 18.35; P, 5.07; S, 5.25. Found: C, 43.69; H, 7.46; N, 18.31; P, 5.11; S, 5.21.

Spectra: IR (Nujol) 728m, 770w, 1110m, 1030m, 1080s, 1115s, 1190s,br, 1235s, 1300m, 1530vs and 1550vs (NH, amide II), 1640vs (C=O, amide I), and 3350s (NH) cm$^{-1}$; $^1$H NMR data given in Table I.

The phosphonium salt is soluble in water, ethanol, 2-propanol, and hot acetonitrile, and insoluble in other common organic solvents.

EXAMPLE 7

Reaction of tetrakis(hydroxymethyl)phosphonium p-toluenesulfonate (16.31 g, 0.05 mol) with 1,3-dimethylurea (17.62 g, 0.2 mol) in toluene (200 ml), following Example 1, gave 27.21 g (89.7%) of tetrakis(1,3-dimethylureidomethyl)phosphonium p-toluenesulfonate (I, R=R'=CH$_3$, R''=H, X=SO$_3$C$_6$H$_4$CH$_3$-p) as a white, crystalline solid, mp 130°–131° C. after two recrystallizations from acetonitrile. The analytical sample was dried under vacuum for 2 hr at 100° C.

Anal. Calcd for $C_{23}H_{43}N_8O_7PS$: C, 45.53; H, 7.14; N, 18.47; P, 5.10; S, 5.28. Found: C, 45.19; H, 7.47; N, 18.25; P, 5.06; S, 5.15.

Spectra: IR (Nujol) 680m, 770w, 816w, 882m, 1010m, 1030m, 1075m, 1115s, 1180s,br, 1230s, 1260m, 1280m, 1540vs,br (NH, amide II), 1625vs (C=O, amide I), and 3300s (NH) cm$^{-1}$; $^1$H NMR data given in Table I.

The phosphonium salt is soluble in water, ethanol, dimethylsulfoxide, and dimethylformamide, and insoluble in other common organic solvents. It can be recrystallized from 2-propanol (9 ml/g) or acetonitrile (40 ml/g).

EXAMPLE 8

Reaction of THPC (9.53 g, 0.05 mol) with 1,1-dimethylurea (17.62 g, 0.2 mol) in toluene (75 ml), following Example 1, gave 23.47 g (99.7%) of tetrakis(3,3-dimethylureidomethyl)phosphonium chloride (I, R=H, R'=R''=CH$_3$, X=Cl) as a colorless, hygroscopic resin.

Spectra: IR (Nujol) 763w, 937w, 1015w, 1220s, 1530vs (NH, amide II), 1645vs (C=O, amide I), and 3300m (NH) cm$^{-1}$; $^1$H NMR data given in Table I; $^{31}$P NMR (H$_2$O) δ 26.4 ppm.

EXAMPLE 9

Reaction of THPC (9.53 g, 0.05 mol) with 2-imidazolidinone (17.22 g, 0.2 mol) in toluene (75 ml), following Example 1, gave 22.23 g (96.1%) of tetrakis[(2-oxo-1-imidazolidinyl)methyl]phosphonium chloride (I, R, R'=CH$_2$CH$_2$, R''=H, X=Cl) as a white solid, mp 220° C. The product was soluble in dilute sodium hydroxide and insoluble in water or organic solvents.

EXAMPLE 10

Reaction of THPC (9.53 g, 0.05 mol) with N-methylurea (14.82 g, 0.2 mol) in toluene (75 ml), following Example 1, gave 20.78 g (100%) of tetrakis(3-methylureidomethyl)phosphonium chloride (I, R=R'=H, R''=CH$_3$, X=Cl) as a brittle amber glass.

Spectra: $^1$H NMR data given in Table I; $^{31}$P NMR (H$_2$O) δ 28.5 ppm.

The phosphonium salt is soluble in water (pH ~7), ethanol, and dimethylsulfoxide, insoluble in ether, chloroform, benzene, and ethyl acetate.

The product, dissolved in water (30 ml), was passed onto a column containing Bio-Rad AG 50W-X4 cation exchange resin (50 g), rinsed with water until chloride-free, and then displaced with 6 N hydrochloric acid, giving 25.52 g (88.3%) of the trihydrochloride as a colorless liquid, n$_D^{20}$ 1.5474.

Anal. Calcd for $C_{12}H_{31}Cl_4O_4P \cdot 3H_2O$: C, 24.92; H, 6.45; Cl, 24.52; N, 19.38; P, 5.36. Found: C, 23.93; H, 7.16; Cl, 22.23; N, 19.07; P, 5.64.

Spectrum: IR (neat) 1560s (NH, amide II), 1640s (C=O, amide I), and 3330s (NH) cm$^{-1}$.

EXAMPLE 11

Reaction of THPC (9.53 g, 0.05 mol) with urea (12.01 g, 0.2 mol) in toluene (75 ml), following Example 1, gave 18.14 g (101%) of tetrakis(ureidomethyl)phosphonium chloride (I, R=R'=R''=H, X=Cl) as a colorless, brittle glass.

Spectra: IR (dmso) 1540s (NH, amide II), 1625m (C=O, amide I), 1680vs (NH$_2$, amide II), and 3350s (NH) cm$^{-1}$; $^1$H NMR data given in Table I; $^{31}$P NMR (H$_2$O) δ 29.5 ppm.

The phosphonium salt is soluble in water (pH 6.9) and dimethylsulfoxide, and insoluble in any of the common organic solvents.

The product, dissolved in water (25 ml), was passed onto a column containing Bio-Rad AG 50W-X4 cation exchange resin (50 g), rinsed with water until chloride-free, and then displaced with 6 N hydrochloric acid, giving 11.21 g (44.5%) of the trihydrochloride as a white solid.

Anal. Calcd for $C_8H_{23}Cl_4N_8O_4P \cdot 2H_2O$: C, 19.06; H, 5.40; Cl, 28.13; N, 22.23; P, 6.14. Found: C, 17.48; H, 6.18; Cl, 28.12; N, 22.03; P, 5.79.

Spectrum: IR (KBr) as above.

EXAMPLE 12

Reaction of 80% THPC (23.82 g, 0.1 mol) with urea (24.02 g, 0.4 mol), following Example 3, gave 36.18 g (100.8%) of tetrakis(ureidomethyl)phosphonium chloride (I, R=R'=R''=H, X=Cl) as a colorless, brittle glass, identical ($^{31}$P NMR) to the product of Example 11.

The outcome was the same when the reflux time was reduced from 2.5 hr to 30 min.

EXAMPLE 13

Reaction of 75% THPS (27.08 g, 0.05 mol) with urea (24.02 g, 0.4 mol), following Example 3, gave 38.89 g (104.7%) of octakis(ureidomethyl)diphosphonium sulfate (I, R=R'=R''=H, X=0.5 SO$_4$) as a pale yellow glass.

Spectra: $^1$H NMR data given in Table I; $^{31}$P NMR (H$_2$O) δ 29.8 ppm.

The decoupled $^{31}$P NMR spectrum revealed the presence of phosphorus-containing impurities in the phosphonium salt region (32.0 to 34.2 ppm) and in the tertiary phosphine oxide region (46.3 to 48.9 ppm), but none in the 0 to −50 ppm region characteristic of tertiary phosphines.

EXAMPLES 14 THROUGH 18

Some ureas contain features which make them undesirable for the preparation of tetrakis(ureidomethyl)-phosphonium salts. Reaction of THPC with 1,1,3-trimethylurea, for example, gave a degradation product, mp 209°–210° C. dec, containing over half of the chlorine. Under milder conditions, with benzene as the azeotroping solvent, reaction ceased when only three mols of water had been displaced, giving a crystalline product, mp 151°–152° C. dec, which retained one hydroxymethyl group (Example 14). Alloxan hydrate and 1,3-diphenylurea both failed to react with THPC in toluene, and decomposed in xylene (Examples 15 and 16). 4,5-Dihydroxy-2-imidazolidinone (DHEU) and 1,3-bis(methoxymethyl)urea both decomposed when heated with THPC in toluene, the former giving a black, tarry mass (Examples 17 and 18).

EXAMPLE 19

A mixture of THPC (19.06 g, 0.1 mol), 1,3-dimethylurea (17.62 g, 0.2 mol), and toluene (150 ml) was heated to reflux in an apparatus fitted with a mechanical stirrer and a Dean-Stark trap for azeotropic removal of the water. The mixture was held at reflux unitl the evolution of water ceased (4 hr); this condensation, as might be expected, required a longer reflux period and more efficient stirring to displace the last of the water than that of Example 1. Half of the 7.2 ml (100.0%) of water was collected during the first 15 min. The product, which separated during the reaction as a mass of white solids, was broken up, triturated under acetonitrile to remove a resinous by-product (4.09 g), filtered, rinsed with acetonitrile and dried, giving 26.21 g (86.3%) of 3,9-dioxo-2,4,8,10-tetramethyl-2,4,8,10-tetraaza-6-phosphoniaspiro[5.5]undecane chloride (II, R=R'=CH$_3$, X=Cl) as a white, crystalline solid. Two recrystallizations from 2-propanol (12 ml/g) gave pure product, mp 161°–162° C. and resolidifying, then mp 217° C. dec.

Anal. Calcd for $C_{10}H_{20}ClN_4O_2P.O.5H_2O$: C, 39.54; H, 6.97; Cl, 11.67; N, 18.45; P, 10.20; mol wt, 304. Found: C, 39.38; H, 6.95; Cl, 11.94; N, 18.33; P, 10.11; mol wt osmometric in $H_2O$), 166, 172.

Spectra: IR (KBr) 757m, 910m, 1035m, 1160m, 1210s, 1250m, 1370m, 1385s, 1410m, 1430m, 1455m, 1490vs, 1660s (C=O, amide I), 2900m, 3000m, and 3500m (OH) cm$^{-1}$; $^1$H NMR data given in Table I; $^{31}$P NMR ($H_2O$) $\delta$ 29.8 ppm.

The phosphonium salt is soluble in water, the lower alcohols, and dimethylsulfoxide, and insoluble in other common organic solvents. It can be recrystallized from 2-propanol or acetonitrile.

EXAMPLE 20

Reaction of THPS (20.31 g, 0.05 mol) with 1,3-dimethylurea (17.62 g, 0.2 mol) in toluene (200 ml), following Example 19, gave 11.72 g, (65.8%) of 3,9-dioxo-2,4,8,10-tetramethyl-2,4,8,10-tetraaza-6-phosphoniaspiro[5.5]undecane bisulfate (II, R=R'=CH$_3$, X=HSO$_4$) as a white, compact crystalline solid, mp 206° C. dec after recrystallization from dimethylformamide (24 ml/g).

Anal. Calcd for $C_{10}H_{21}N_4O_6PS$: C, 33.70; H, 5.94; N, 15.73; P, 8.69; S, 9.00. Found: C, 33.53; H, 6.26; N, 15.66; P, 8.57; S, 8.84.

Spectra: IR (Nujol) 742m, 754m, 775m, 825s, 854w, 900m, 1030s, 1050s, 1150vs, 1200s, 1220s, 1295s, 1655vs (C=O, amide I) cm$^{-1}$; $^1$H NMR data given in Table I.

The phosphonium salt is soluble in water and insoluble in the common organic solvents. It can be recrystallized from either dimethylformamide or dimethylsulfoxide. Like the product of Example 5, it contained only one of the two phosphorus atoms of the THPS.

EXAMPLE 21

Reaction of tetrakis(hydroxymethyl)phosphonium benzenesulfonate (31.23 g, 0.1 mol) with 1,3-dimethylurea (17.62 g, 0.2 mol) in toluene (100 ml), following Example 19, gave 46.30 g of 3,9-dioxo-2,4,8,10-tetramethyl-2,4,8,10-tetraaza-6-phosphoniaspiro[5.5]undecane benzenesulfonate (II, R=R'=CH$_3$, X=SO$_3$C$_6$H$_5$) as a caramel-colored, low-melting solid.

EXAMPLE 22

A mixture of THPC (9.53 g, 0.05 mol), urea (6.01 g, 0.1 mol), and toluene (25 ml) was heated to reflux in an apparatus fitted with a Dean-Stark trap for azeotropic removal of the water. After 2 hr, 2.6 ml (72%) of water had been collected and evolution ceased. The product, which had separated during the reaction as a foamy white solid, was broken up, filtered, triturated under water and filtered again, giving 12.02 g (97.1%) of poly[bis(ureylenedimethyl)phosphonium chloride] (III, R=H, X=Cl) as a brittle white solid, dec 230° C.

Anal. Calcd for $C_6H_{12}ClN_4O_2P.O.5H_2O$: C, 29.10; H, 5.29; Cl, 14.32; N, 22.63; P, 12.51. Found: C, 28.96; H, 5.26; Cl, 14.10; N, 22.71; P, 12.39.

Spectra: IR (KBr) 1010m, 1250s,br, 1380m, 1560vs (NH, amide II), 1660vs (C=O, amide I), 3000m, and 3430vs (NH) cm$^{-1}$; ESCA data given in Table II.

With benzene as the solvent, 2.1 ml of water was displaced but the bulk of the product remained water-soluble.

TABLE II

| | | ESCA Spectra of Phosphonium Salts | | | | | |
|---|---|---|---|---|---|---|---|
| Example | Structure | Binding Energy, eV | | | | | |
| | | $P_{2p}$ | $Cl_{2p}$ | $C_{1s}$ (CH$_2$) | $C_{1s}$ (C=O) | $N_{1s}$ | $O_{1s}$ |
| 22 | III | 131.7 | 196.9 | 283.9 | 287.9 | 398.9 | 531.0 |
| 25 | III | 132.3 | 197.3 | 284.7 | 288.5 | 399.1 | 532.1 |
| 27 | V | 131.7 | 196.9 | 284.3 | 287.9 | 399.0 | 530.6 |

EXAMPLE 23

A mixture of 80% THPC (59.56 g, 0.25 mol) and urea (30.03 g, 0.5 mol) was heated to reflux in an oil bath. The urea dissolved at 100° C., giving a clear, colorless solution. A mildly exothermic reaction ensued, with steady refluxing, but within 10 min the mixture thickened and set up to a foamy gel. After cooling, the product was triturated under water, filtered, and dried over phosphorus pentoxide in a vacuum desiccator, giving 60.34 g (97.5%) of poly[bis(ureylenedimethyl)phosphonium chloride] (III, R=H, X=Cl) as a friable white solid, dec 230° C.

Anal. Calcd for $C_6H_{12}ClN_4O_2P.O.5H_2O$: C, 29.10; H, 5.29; Cl, 14.32; N, 22.63; P, 12.51. Found: C, 28.98; H, 5.32; Cl, 14.08; N, 22.67; P, 12.25.

Spectrum: IR (KBr) identical to Example 22.

EXAMPLE 24

Reaction of 75% THPS (54.17 g, 0.1 mol) with urea (24.02 g, 0.4 mol), following Example 23, gave 51.80 g (99.6%) of poly[tetrakis(ureylenedimethyl)disphosphonium sulfate] (III, R=H, X=0.5 SO$_4$) as a friable white solid, dec 220° C.

Anal. Calcd for $C_{12}H_{24}N_8O_8P_2S.H_2O$: C, 27.69; H, 5.04; N, 21.54; P, 11.90; S, 6.16. Found: C, 28.01; H, 5.18; N, 21.45; P, 9.73; S, 5.19.

EXAMPLE 25

Reaction of THPC (9.53 g, 0.05 mol) with N-methylurea (7.41 g, 0.1 mol) in toluene (75 ml), following Example 22, gave 14.02 g (101.7%) of poly[bis(N-methylureylenedimethyl)phosphonium chloride] (III, R=CH$_3$, X=Cl) as a friable white solid, mp 210° C. dec.

Anal. Calcd for C$_8$H$_{16}$ClN$_4$O$_2$P.0.5H$_2$O: C, 34.85; H, 6.22, Cl, 12.86; N, 20.33; P, 11.23. Found: C, 34.75; H, 6.10; Cl, 12.74; N, 20.19; P, 11.07.

Spectra: IR (KBr) 940w, 1030m, 1220m, 1550s (NH, amide II), 1660s (C=O, amide I), and 3450vs (NH) cm$^{-1}$; ESCA data given in Table II.

EXAMPLE 26

Reaction of THPC (19.06 g, 0.1 mol) with 1,3-dimethylurea (26.44 g, 0.3 mol) in toluene (75 ml), following Example 19, gave 25.85 g (67.5%) of 5,5-bis(1,3-dimethylureidomethyl)-1,3-dimethyl-2-oxo-1,3-diaza-5-phosphoniacyclohexane chloride (IV, R=R'=CH$_3$, X=Cl) as a white, crystalline solid, mp 191°-192.5° C. dec. The remainder (11.89 g) was a viscous yellow oil. Two recrystallizations from 2-propanol (5 ml/g), followed by thorough drying in a vacuum at 100° C., gave pure product, mp 196°-197° C. dec.

Anal. Calcd for C$_{13}$H$_{28}$ClN$_6$O$_3$P: C, 40.78; H, 7.37; Cl, 9.26; N, 21.96; P, 8.09; mol wt, 383. Found: C, 40.43; H, 7.04; Cl, 8.95; N, 21.83; P, 8.06; mol wt (osmometric in H$_2$O), 234.

Spectra: IR (Nujol) 902s, 1140m, 1150m, 1195m, 1240m, 1255m, 1530s (NH, amide II), 1580vs, 1670s (C=O, amide I) and 3230s (NH) cm$^{-1}$; $^1$H NMR data given in Table I.

The phosphonium salt is soluble in water and the lower alcohols, and insoluble in other common organic solvents.

EXAMPLE 27

Reaction of 80% THPC (23.82 g, 0.1 mol) with urea (18.02 g, 0.3 mol), following Example 23, gave 25.00 g (83.7%) of poly[bis(ureidomethyl) (ureylenedimethyl)phosphonium chloride] (V, R=H, X=Cl) as a friable pale yellow gel, dec 208° C.

Anal. Calcd for C$_7$H$_{16}$ClN$_6$O$_3$P: C, 28.15; H, 5.40; Cl, 11.87; N, 28.14; P, 10.37. Found: C, 27.93; H, 6.05; Cl, 11.63; N, 27.64; P, 10.41.

Spectra: IR (KBr) 1020w, 1150m, 1245s, 1350s, 1380m, 1550vs (NH, amide II), 1670vs (C=O, amide I), 2970w, and 3430vs (NH) cm$^{-1}$; ESCA data given in Table II.

EXAMPLE 28

A solution of tetrakis(ureidomethyl)phosphonium chloride (35.88 g, 0.1 mol; see Example 11) in water (15 ml) was heated to reflux and treated with 80% THPC (23.82 g, 0.1 mol) in a single portion. The solution started to thicken after 6 min and gelled after 12 min, immobilizing the stirrer. After heating at reflux for another 30 min, the product was cooled, triturated under water, filtered, and dried to constant weight in a vacuum oven at 80° C., giving 46.63 g (94.1%) of poly[bis(ureylenedimethyl)phosphonium chloride] (III, R=H, X=Cl) as a friable off-white solid, dec 230° C.

Spectrum: IR (KBr) identical to Example 22.

EXAMPLE 29

A mixture of poly[bis(ureylenedimethyl)phosphonium chloride] (2.48 g, 0.01 mol; see Example 22), urea (1.20 g, 0.02 mol), and water (5 ml) was heated to reflux in an oil bath. The polymer gradually dissolved over a 2 hr period. After heating for 1 hr more the solution was cooled, stripped in a rotary evaporator, and thoroughly dried in a vacuum desiccator, giving 3.55 g (98.9%) of tetrakis(ureidomethyl)phosphonium chloride (I, R=R'=R''=H, X=Cl) as a pale yellow, brittle glass.

Spectra: IR (dmso) identical to Example 11; $^1$H NMR (D$_2$O)δ 4.30 (doublet, CH$_2$, J=4.0 Hz) ppm.

This reaction can be carried out with excess urea, but the latter is difficult to separate from the product.

EXAMPLE 30

Reaction of poly[tetrakis(ureylenedimethyl)diphosphonium sulfate] (10.15 g, 0.02 mol; see Example 24) with urea (4.80 g, 0.08 mol) in water (20 ml), following Example 29, gave 14.80 g (99.7%) of octakis(ureidomethyl)diphosphonium sulfate (I, R=R'=R''=H, X=0.5 SO$_4$) as a pale yellow glass.

Spectrum: $^1$H NMR identical to Example 13.

EXAMPLE 31

A solution of 75% THPS (1083.4 g, 2 mols) in water (1000 ml) was heated in a 3000 ml beaker in a water bath (90° C.) and treated with small portions of urea (961.0 g, 16 mols) over a 3 hr period, with occasional hand stirring by means of a spatula. The gel was too thick to be stirred by a magnetic or mechanical stirrer. Each portion of urea produced an endotherm followed by a mild exotherm. The mixture, thick with gel, was heated 4 hr in the boiling water bath followed by 3 hr on a hot plate, stirring from time to time and adding water as needed. At the end, only a few gel particles remained and the solution was neutral (pH 7.05). The product, octakis-(ureidomethyl)diphosphonium sulfate (I, R=R'=R''=H, X=0.5 SO$_4$), was identical to that of Example 13.

EXAMPLE 32

A mixture of 3,9-dioxo-2,4,8,10-tetramethyl-2,4,8,10-tetraaza-6-phosphoniaspiro[5.5]undecane chloride (2.95 g, 0.01 mol; see Example 19), 1,3-dimethylurea (1.76 g, 0.02 mol) and acetonitrile (5 ml) was heated to reflux in an oil bath, whereupon all of the solids dissolved. The solution was held at reflux for 2 hr, cooled, and stripped under vacuum, leaving 4.91 g of product that gradually solidified. The product was extracted with benzene in a Soxhlet extractor to remove the excess 1,3-dimethylurea and stripped again, giving 3.45 g (90.1%) of 5,5-bis(1,3-dimethylureidomethyl)-1,3-dimethyl-2-oxo-1,3-diaza-5-phosphoniacyclohexane chloride (IV, R=R'=CH$_3$, X=Cl) as a white, crystalline solid. One recrystallization from 2-propanol gave pure product, mp 194°-195° C. dec.

Spectra: IR, $^1$H NMR identical to Example 26.

EXAMPLE 33

A solution of sodium iodide (3.00 g, 0.02 mol) in ethanol (80 ml) was treated with tetrakis(1,3-dimethylureidomethyl)phosphonium chloride (9.42 g, 0.02 mol; see Example 1) in small portions, stirred 2 hr at room temperature, heated to boiling, filtered hot to remove the sodium chloride (0.83 g, 70.9%, giving a negative test for iodide with acidified iodate), concentrated to small volume and filtered again, giving 9.03 g (80.3%) of tetrakis(1,3-dimethylureidomethyl)phosphonium iodide (I, R=R'=CH$_2$, R"=H, X=I) as a white, crystalline solid, mp 193°-194° C. dec. One recrystallization from ethanol gave pure product, mp 194° C. dec.

Anal. Calcd for C$_{16}$H$_{36}$IN$_8$O$_4$P: I, 22.56; P, 5.51. Found: I, 22.78; P, 5.56.

Spectra: IR, $^1$H NMR identical to Example 4.

EXAMPLE 34

Picric acid (0.69 g, 3.0 mmol) was added to a solution of tetrakis-(1,3-dimethylureidomethyl)phosphonium chloride (1.41 g, 3.0 mmol; see Example 1) in water (15 ml), heated to boiling, and allowed to cool. The product, tetrakis(1,3-dimethylureidomethyl)phosphonium hydrogen dipicrate (I, R=R'=CH$_3$, R"=H, X=OC$_6$H$_2$(NO$_2$)$_3$), separated as a mass of bright yellow needles (1.01 g, 72.5%), mp 101°-102° C. One recrystallization from chloroform gave an analytical sample, mp 101°-102° C.

Anal. Calcd for C$_{28}$H$_{41}$N$_{14}$O$_{18}$P.2H$_2$O: C, 36.21; H, 4.88; Cl, none; N, 21.11; P, 3.33. Found: C, 35.58; H, 4.81; Cl, none; N, 21.12; P, 3.36.

Spectra: IR (Nujol) 705w, 718m, 738m, 765m, 783w, 892w, 917m, 1075m, 1160s, 1235s, 1300s, 1410m, 1550vs (NH, amide II) 1640s (C=O, amide I), and 343m (NH) cm$^{-1}$; $^1$H NMR data given in Table I.

The phosphonium salt is soluble in acetone, 2-propanol, and hot water, and insoluble in benzene and carbon tetrachloride.

EXAMPLE 35

A solution of barium chloride (3.16 g, 15 mmol) in water (25 ml) was added to a solution of tetrakis(1,3-dimethylureidomethyl)phosphonium bisulfate (5.64 g, 10 mmol; see Example 5) in water (25 ml), causing an immediate separation of solids. The mixture was boiled briefly, cooled, and filtered, giving 2.35 g (10.1 mmol) of barium sulfate. The filtrate, stripped and extracted with 2-propanol, yielded 1.03 g (4.9 mmol) of barium chloride. The extract, stripped, neutralized with aqueous sodium bicarbonate and recrystallized from 2-propanol, yielded 2.80 g (52.7%) of the 1:1 solvate of tetrakis(1,3-dimethylureidomethyl)phosphonium chloride (I, R=R'=CH$_3$, R"=H, X=Cl) and 2-propanol as a white, crystalline solid, mp 191°-192° C. dec.

Spectrum: IR identical to 1:1 solvate in Example 1.

EXAMPLES 36 THROUGH 39

Urea/THPC formulations having molar ratios of 1:1, 2:1, 3:1, and 4:1 were applied to cotton fabric by the pad/dry/cure method. Each formulation, comprising 80% THPS (15.01 g, 63 mmol), urea (63, 126, 189 or 252 mmol), Triton X-100 (0.1 g), and sufficient water to make 75 g of solution, was heated to 75°-80° C. for 30 min to effect a partial condensation (since all but the 4:1 formulation gelled within 10 min at 100° C.) The pH increased with the urea concentration (Table III). A desired, scoured, and bleached 80×80 cotton printcloth was padded through each formulation to an 80-90% wet pickup, dried at 85° C. for 4 min, and cured at 160° C. for 4 min in a forced draft oven, rinsed in hot running tap water for 15 min, and line dried. The results are given in Table III.

TABLE III

Application of Urea/THPC Finish to Cotton at Various Mole Ratios

| Example | Mole Ratio | pH | % Add-on | % P | % N | % Cl |
|---|---|---|---|---|---|---|
| 36 | 1:1 | 2.0 | 6.9 | 1.55 | 1.66 | 0.03 |
| 37 | 2:1 | 2.2 | 9.9 | 1.28 | 2.34 | 0 |
| 38 | 3:1 | 2.2 | 2.4 | 0.29 | 0.57 | 0 |
| 39 | 4:1 | 2.6 | 0.7 | 0 | 0.18 | 0 |

Under these conditions the chlorine was in fact lost, even though no base had been used. The fabric treated with the 1:1 formulation was badly discolored. The highest add-on was achieved with the 2:1 formulation, corresponding to structure III (R=H, X=Cl), and the lowest add-on with the 4:1 formulation, corresponding to structure I (R=R'=R"=H, X=Cl).

Application of the 2:1 formulation to cotton printcloth at curing temperatures ranging from 90° C. to 160° C. resulted in little polymer fixation at temperatures below 140° C. Clearly, the application of urea/THPC formulations to cotton under the standard pad/dry/cure conditions used for THPC/amide finishing does not achieve the objects of this invention, which require that the quaternary structure of the phosphonium salts be preserved.

EXAMPLES 40 THROUGH 44

A urea/THPS formulation was prepared by mixing 75% octakis(ureidomethyl)diphosphonium sulfate (39.09 g, 40.3 mmol; see Example 13) with 75% THPS (21.84 g, 40.3 mmol) and Triton X-100 (0.1 g), and making up to 100 g with water. The formulation was applied to desized, scoured, and bleached 80×80 cotton printcloth to a 100-110% wet pickup, cured at 100° C. in a forced draft oven for the time indicated, rinsed in hot running tap water for 15 min, and line dried. The results are given in Table IV.

TABLE IV

Application of Urea/THPS Finish to Cotton. Effect of Cure Time

| Example | Cure Time, min. | % Add-on | % P | % N | % S |
|---|---|---|---|---|---|
| 40 | 2 | 7.4 | 0.38 | 0.84 | 0.15 |
| 41 | 4 | 22.6 | 1.62 | 4.06 | 0.69 |
| 42 | 8 | 34.9 | 2.98 | 5.56 | 1.06 |
| 43 | 16 | 37.5 | 2.96 | 5.66 | 1.05 |
| 44 | 32 | 40.6 | 3.29 | 6.09 | 1.12 |

Under these conditions, a cure time of 8 min was sufficient. There was little loss of quaternary structure, since most of the sulfur was retained.

EXAMPLES 45 THROUGH 52

Application of the urea/THPS finish to cotton printcloth, following Example 42 but varying the cure temperature instead of the cure time, gave the results shown in Table V.

TABLE V

Application of Urea/THPS Finish to Cotton. Effect of Cure Temperature

| Example | Cure Temp. °C. | % Add-on | % P | % N | % S |
|---|---|---|---|---|---|
| 45 | 55 | 1.2 | 0.10 | 0.13 | 0.02 |
| 46 | 70 | 1.8 | 0.09 | 0.07 | 0.02 |
| 47 | 85 | 4.9 | 0.39 | 0.94 | 0.19 |
| (42) | (100) | (34.9) | (2.98) | (5.56) | (1.06) |
| 48 | 115 | 41.4 | 3.41 | 6.24 | 1.03 |

TABLE V-continued
Application of Urea/THPS Finish to Cotton.
Effect of Cure Temperature

| Example | Cure Temp. °C. | % Add-on | % P | % N | % S |
|---|---|---|---|---|---|
| 49 | 130 | 46.6 | 3.70 | 6.54 | 1.10 |
| 50 | 145 | 49.6 | 3.82 | 6.07 | 1.12 |
| 51 | 160 | 47.7 | 3.75 | 6.71 | 1.28 |
| 52 | 175 | 51.5 | 3.71 | 6.15 | 1.28 |

Below 100° C. little of the finish was retained, and at 160° C. or above the fabric yellowed and tendered. These results were verified by interpolation.

EXAMPLES 53 THROUGH 57

A urea/THPS formulation was prepared by mixing 75% THPS (43.68 g, 80.6 mmol) with urea (19.36 g, 322.4 mmol) and Triton X-100 (0.1 g), and making up to 100 g with water. The formulation was applied to desized, scoured, and bleached 80×80 cotton printcloth to a 100–110% wet pickup, cured at 100° C. in a forced draft oven for the time indicated, rinsed in hot running tap water for 15 min, and line dried. The results are given in Table VI.

TABLE VI
Application of Urea/THPS Finish to Cotton.
Effect of Cure Time

| Example | Cure Time, min. | % Add-on | % P | % N | % S |
|---|---|---|---|---|---|
| 53 | 2 | 0.6 | 0.05 | 0.03 | 0 |
| 54 | 4 | 1.7 | 0.09 | 0.05 | 0 |
| 55 | 8 | 19.5 | 1.90 | 3.72 | 0.81 |
| 56 | 16 | 30.5 | 2.51 | 4.95 | 1.07 |
| 57 | 32 | 38.9 | 3.02 | 6.08 | 1.22 |

A finish comparable to Example 42 was obtained when the cure time was 32 min. Clearly, the polymer gel formed much more slowly on cotton when the reagents were applied ab initio than when they were partially condensed prior to application.

I claim:

1. A quaternary ureidomethyl phosphonium salt having the formula

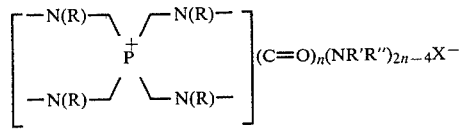

where R, R' and R" are radicals selected from the group consisting of hydrogen, alkyl, and substituted alkyl, n is an integer from 2 to 3, and X is an acid radical.

2. A quaternary ureidomethyl phosphonium salt in accordance with claim 1 wherein n is 2.

3. A quaternary ureidomethyl phosphonium salt in accordance with claim 1 wherein n is 3.

4. A process for preparing a quaternary ureidomethyl phosphonium salt which comprises condensing a urea having the formula RNHC(O)NR'R", where R, R' and R" are radicals selected from the group consisting of hydrogen, alkyl, and substituted alkyl, with a quaternary hydroxymethyl phosphonium salt having the formula $(HOCH_2)_4P^+X^-$, where X is an acid radical, in a molar ratio of from 2:1 to 3:1, and revovering the product from the resulting reaction mixture.

5. A process in accordance with claim 4 wherein the molar ratio is 2:1.

6. A process in accordance with claim 4 wherein the molar ratio is 3:1.

7. A process for preparing a quaternary ureidomethyl phosphonium salt which comprises condensing a urea having the formula $RNHC(O)NH_2$, wherein R is a radical selected from the group consisting of hydrogen, alkyl, and substituted alkyl, with a quaternary ureidomethyl phosphonium salt having the formula

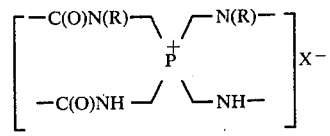

wherein R is similarly defined and X is acid radical, in a molar ratio of at least 2:1, and recovering the product from the resulting reaction mixture.

8. A process in accordance with claim 7 wherein R is H and X is sulfate.

9. A quaternary ureidomethyl phosphonium salt having the formula

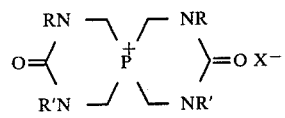

wherein R and R' are radicals selected from the group consisting of alkyl and substituted alkyl, and X is an acid radical.

10. A quaternary ureidomethyl phosphonium salt in accordance with claim 9 wherein R and R' are both methyl.

11. A quaternary ureidomethyl phosphonium salt in accordance with claim 9 wherein X is a radical selected from the group consisting of chloride, bisulfate, and benzenesulfonate.

12. A process for preparing a quaternary ureidomethyl phosphonium salt which comprises condensing a urea having the formula RNHC(O)NHR', where R and R' are radicals selected from the group consisting of alkyl and substituted alkyl, with a quaternary hydroxymethyl phosphonium salt having the formula $(HOCH_2)_4P^-X^-$, where X is an acid radical, in a molar ratio of approximately 2:1, and recovering the product from the resulting reaction mixture.

13. A quaternary ureidomethyl phosphonium salt having the formula

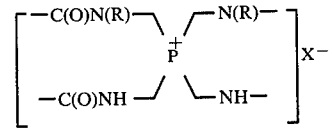

wherein R is a radical selected from the group consisting of hydrogen, alkyl, and substituted alkyl, and X is an acid radical.

14. A quaternary ureidomethyl phosphonium salt in accordance with claim 13 wherein R is hydrogen.

15. A quaternary ureidomethyl phosphonium salt in accordance with claim 13 wherein R is methyl.

16. A quaternary ureidomethyl phosphonium salt in accordance with claim 13 wherein X is a radical selected from the group consisting of chloride and sulfate.

17. A process for preparing a quaternary ureidomethyl phosphonium salt which comprises condensing a urea having the formula RNHC(O)NH$_2$, where R is a radical selected from the group consisting of hydrogen, alkyl, and substituted alkyl, with a quaternary hydroxymethyl phosphonium salt having the formula (HOCH$_2$)$_4$P$^-$X$^-$, where X is an acid radical, in a molar ratio approximately 2:1, and recovering the product from the resulting reaction mixture.

18. A process for preparing a quaternary ureidomethyl phosphonium salt which comprises condensing a quaternary ureidomethyl phosphonium salt having the formula

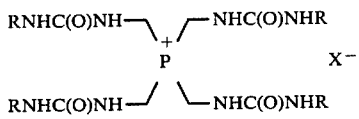

wherein R is a radical selected from the group consisting of hydrogen, alkyl, and substituted alkyl and X is an acid radical, with a quaternary hydroxymethyl phosphonium salt having the formula (HOCH$_2$)$_4$P$^+$X$^-$, wherein X is similarly defined, in a molar ratio of approximately 1:1, and recovering the product from the resulting reaction mixture.

19. A quaternary ureidomethyl phosphonium salt having the formula

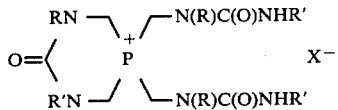

wherein R and R' are radicals selected from the group consisting of alkyl and substituted alkyl, and X is an acid radical.

20. A quaternary ureidomethyl phosphonium salt in accordance with claim 19 wherein R and R' are both methyl and X is chloride.

21. A process for preparing a quaternary ureidomethyl phosphonium salt which comprises condensing a urea having the formula RNHC(O)NHR', wherein R and R' are radicals selected from the group consisting of alkyl and substituted alkyl, with a quaternary hydroxymethyl phosphonium salt having the formula (HOCH$_2$)$_4$P$^+$X$^-$, wherein X is an acid radical, in a molar ratio of approximately 3:1, and recovering the product from the resulting reaction mixture.

22. A process for preparing a quaternary ureidomethyl phosphonium salt which comprises condensing a urea having the formula RNHC(O)NHR', wherein R and R' are radicals selected from the group consisting of alkyl and substituted alkyl, with a quaternary ureidomethyl phosphonium salt having the formula

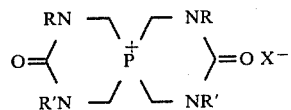

wherein R and R' are similarly defined and X is an acid radical, in a molar ratio of at least 1:1, and recovering the product from the resulting reaction mixture.

23. A quaternary ureidomethyl phosphonium salt having the formula

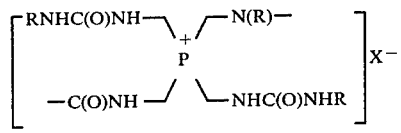

wherein R is a radical selected from the group consisting of hydrogen, alkyl, and substituted alkyl, and X is an acid radical.

24. A quaternary ureidomethyl phosphonium salt in accordance with claim 23 wherein R is hydrogen and X is chloride.

25. A process for preparing a quaternary ureidomethyl phosphonium salt which comprises condensing a urea having the formula RNHC(O)NH$_2$, wherein R is a radical selected from the group consisting of hydrogen, alkyl, and substituted alkyl, with a quaternary hydroxymethyl phosphonium salt having the formula (HOCH$_2$)$_4$P$^-$X$^-$, wherein X is an acid radical, in a molar ratio of approximately 3:1, and recovering the product from the resulting reaction mixture.

* * * * *